United States Patent
Melvin

(12) 
(10) Patent No.: US 6,214,047 B1
(45) Date of Patent: Apr. 10, 2001

(54) ARTICLE AND METHOD FOR COUPLING MUSCLE TO A PROSTHETIC DEVICE

(75) Inventor: David B. Melvin, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/037,821

(22) Filed: Mar. 10, 1998

(51) Int. Cl.[7] .................................. A61F 2/02; A61F 2/08
(52) U.S. Cl. ........................................ 623/11.11; 623/13.11
(58) Field of Search .................. 623/11, 13, 14, 623/3

(56) References Cited

U.S. PATENT DOCUMENTS

| | | | |
|---|---|---|---|
| 3,176,316 | * | 4/1965 | Bodell ................................... 623/13 |
| 4,149,277 | * | 4/1979 | Bokros .................................. 623/13 |
| 4,187,558 | * | 2/1980 | Dahlen et al. ........................... 3/1 |
| 4,453,537 | | 6/1984 | Spitzer . |
| 4,585,458 | * | 4/1986 | Kurland ................................ 623/13 |
| 4,846,831 | | 7/1989 | Skillin . |
| 4,917,700 | * | 4/1990 | Aikins .................................. 623/13 |
| 4,946,377 | * | 8/1990 | Kovach ................................ 623/13 |
| 4,964,414 | * | 10/1990 | Handa et al. ......................... 128/784 |
| 5,217,495 | * | 6/1993 | Kaplan et al. .......................... 623/13 |
| 5,443,504 | * | 8/1995 | Hill ........................................ 623/3 |
| 5,456,715 | * | 10/1995 | Liotta ...................................... 623/3 |
| 5,981,827 | * | 11/1999 | Devlin et al. .......................... 623/16 |

OTHER PUBLICATIONS

Farrar et al (1992), *Journal of Heart and Lung Transplantation*, pp. S341–S349.
Farrar et al, *Skeletal Muscle Power Source*, pp. M481–M484.
Sasaki et al (1992), *ASAIO Journal*, pp. M507–M511.
Reichenbach et al (1997), *ASAIO Journal*, pp. M359–M363.
Acker et al (1987), *Science*, vol. 236, pp. 324–326.
Salmons et al (1992), *British Heart Journal*, vol. 68, pp. 333–338.
Ugolini (1986), *Biomechanical Cardiac Assist*, pp. 193–211.
Reichenbach et al (1997), *ASAIO Journal*, vol. 43, pp. M668–M672 (and Abstract).

* cited by examiner

Primary Examiner—David J. Isabella
Assistant Examiner—Alvin Stewart
(74) Attorney, Agent, or Firm—Dinsmore & Shohl LLP

(57) ABSTRACT

A prosthetic linkage for use with skeletal muscle. The linkage includes a plurality of longitudinally extending filaments forming a strand. The strand has a first portion that includes a core portion wherein the filaments extend generally parallel to each other, and an exterior portion wherein the filaments are braided along its longitudinal axis around the core portion. The strand also includes a second portion wherein the filaments are generally randomly oriented and sized for integration into skeletal muscle.

22 Claims, 2 Drawing Sheets

ARTICLE AND METHOD FOR COUPLING MUSCLE TO A PROSTHETIC DEVICE

TECHNICAL FIELD OF THE INVENTION

The present invention relates to a device and method for coupling skeletal muscle to a prosthetic device or bone and more specifically, a device and method for providing a mechanical linkage to actuate a prosthetic device or bone in response to skeletal muscle contraction.

BACKGROUND OF THE INVENTION

The natural heart, and specifically, the cardiac muscle tissue of the natural heart (e.g., myocardium) can fail for various reasons to a point where the natural heart cannot provide sufficient circulation of blood for a body so that life can be maintained or can completely fail. Heart failure can be due to a variety of causes and/or reasons, including viral disease, idiopathic disease, valvular disease (mitral, aortic and/or both), ischemic disease, Chagas' disease and so forth. As a solution for the dysfunctional, failing and/or diseased natural heart, attempts have been made in the past to provide a treatment and/or device to assist in or entirely maintain blood circulation.

One approach to treat a failing heart has been to transplant a heart from another human or animal into a patient. The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk exists that the recipient's body will reject the transplanted organ and attack it as a foreign object. Moreover, the number of potential donor hearts is far less than the number of patients in need of a transplant. Although use of animal hearts would lessen the problem with fewer donors than recipients, there is an enhanced concern with rejection of the animal heart.

Another treatment and therapy for congestive heart failure has been to wrap skeletal muscle around the epicardial surface of the patient's own heart. Skeletal muscle can be an alternative to electromechanical systems (e.g., artificial hearts and/or ventricular assist devices), and thus may eliminate the need for an external power sources and/or skin penetrating power sources. In a cardiomyoplasty procedure, skeletal muscle, such as the latissimus dorsi muscle from the back, can be surgically removed from its natural anatomical position, such as across the back in the case of the latissimus dorsi muscle. Then, it is wrapped around the heart, allowed to heal, and reconditioned from a fast twitch muscle, which is susceptible to fatigue, into muscle with slow-twitch muscle fibers capable of chronic periodic contractions and that is generally fatigue resistant.

Use of a skeletal muscle wrap to power an existing natural heart has several drawbacks. Vascular interruption to the skeletal muscle while it is being removed and transplanted around the heart can lead to muscle degeneration and can adversely affect its ability to contract with sufficient force. Skeletal muscle typically requires a pre-load stretching in order to contract with sufficient force. In order to sufficiently pre-load stretch the skeletal muscle wrap, the heart has to be expanded, sometime to levels or positions that are unhealthy. This can be especially true during the end diastolic phase when the chambers of the heart are still filling with blood. Chronic overexpansion of the heart can lead to ischemic disease. Sufficient contraction of the skeletal muscle wrap does not actively occur every heart beat, and it may only occur every second or third heart beat. Moreover, a single muscle generally cannot provide sufficient contraction (e.g., pumping force) to meet cardiac stroke requirements for circulation of blood. As such, even after a skeletal wrap has been reconditioned as mentioned above, it can usually only generate enough pumping force to augment the heart's naturally occurring pumping action and thus, usually cannot replace the pumping action of the heart.

Another approach has been to either replace the existing natural heart in a patient with an artificial heart or a ventricular assist device or to affix a pump-like device in and/or around the existing natural heart. These circulatory assist devices must be powered by a source which can be external to the body. External power sources are not typically restrained by size, and sometimes can be large and/or bulky, which can decrease a patient's mobility. This can be the case even when a portable system is used for a short period of time. Some power sources, which are external to the body, power or actuate the internal device via cables, electrical cords and/or pneumatic hoses. Indefinitely having percutaneous connectors, which break through the skin, can enhance the onset of infections. A circulatory assist device can be powered by electrical power that is transmitted to the circulatory assist device using a transformer to transmit power transcutaneously through the skin. Such a power delivery system also can have drawbacks. Power to the circulatory assist device can be interrupted if the coils of the transformer become displaced from each other. Also, electrical conductors can also increase the possibility of cross coupling which can lead to power disruption because of a magnetic flux. Drawbacks on powering and delivering power to these circulatory assist devices have limited use of these devices to applications having too brief a time period to provide a real lasting benefit.

Others have suggested leaving skeletal muscle in situ and using it to power a circulatory assist device by delivering a force, due to unidirectional or linear shortening of the muscle's myofibers, by a linkage, such as a rod, cable, suture or cord having a plurality of bundled or braided fibers along its entire length. However, repeated and indefinite transmission of contractible force from muscle to an artificial device using such a linkage presents difficulties which have not been addressed. Due to repeated use, the suture would deliver significant pressure to the linkage/muscle interface, which already has a reduced blood supply. Chronic repetition of such high pressure may likely harm tissue integrity. Also, the suture would likely reposition itself closer to the distal end of the muscle since the muscle will likely remodel around the suture due to the high pressure. As such, a sufficient bond between the suture and muscle to sustain muscle contract force may not develop. This failure to establish the bond and the deteriorating condition may eventually lead to the suture becoming unattached from the muscle and failing.

As can be seen, currently available treatments, procedures, and devices for maintaining blood circulation have a number of shortcomings that contribute to the complexity of the procedure or device. The current devices and procedures are in limited supply, can be extremely invasive, and may only provide a benefit for a brief period of time. A need exists in the industry for an artificial coupling that can be used to harness the force and power of skeletal muscle in situ whereby an artificial circulation support device can be powered (e.g., pumped or otherwise actuated) repeatedly and indefinitely.

SUMMARY OF THE PRESENT INVENTION

It is the object of the present invention to provide a device and method for treating cardiomyopathies that addresses and overcomes the above-mentioned problems and shortcomings in the thoracic medicine art.

Another object of the present invention is to provide a device and method for coupling skeletal muscle to a prosthetic device or bone that maximizes the linear force potential of skeletal muscle.

Yet another object of the present invention is to provide a device and method for coupling skeletal muscle to a prosthetic device or bone that leaves the skeletal muscle generally in situ.

Still another object of the present invention is to provide a device and method for coupling skeletal muscle to a prosthetic device or bone that eliminates the need for an external power supply.

It is another object of the present invention is to provide a device and method for coupling skeletal muscle to a prosthetic device or bone that can harness and utilize more than one muscle group synchronously.

Yet another object of the present invention is to provide a device and method for coupling skeletal muscle to a prosthetic device that can provide a selectable contraction rate for the heart.

A further object of the present invention is to provide a device and method for coupling skeletal muscle to a prosthetic device that can provide independent control of the duration of muscle contraction and blood ejection from the heart.

It is yet another object of the present invention is to provide a device and method for coupling skeletal muscle to a prosthetic device or bone that can repeatedly provide for transmission of contractile force from skeletal muscle to a prosthetic device.

Another object of the present invention is to provide a device and method for use with a circulatory assist device that is free from an external energy source.

Still a further object of the present invention is to provide a device and method for coupling skeletal muscle to a prosthetic device that can provide for independent control of skeletal muscle pre-load and end diastolic pressure of the heart.

Additional objects, advantages, and other features of the present invention will be set forth and will become apparent to those skilled in the art upon examination of the following, or may be learned with practice of the invention.

To achieve the foregoing and other objects, and in accordance with the purpose herein, the present invention comprises a prosthetic coupling for use with skeletal muscle. The strand of the coupling includes a plurality (greater than 5,000) of longitudinally extending filaments, such as polyester fiber, forming a strand. The strand has a first portion that includes a core portion wherein the filaments extend generally parallel to each other, and an exterior portion wherein the filaments are braided along its longitudinal axis around the core portion. The strand also includes a second portion wherein the filaments are generally randomly oriented and sized for integration into skeletal muscle. Preferably, the length of the filaments of the second portion is greater than about 40 mm.

A non-adhering sheath, preferably made from polyurethane, for covering a portion of the strand can also be provided. The sheath can include a tubular shaped portion for covering part or all of the first portion, and a generally frustoconically shaped portion configured for covering the terminal end or distal portion of the muscle where the second portion has been embedded.

A junctional device can be provided adjacent the end of the first portion for assisting in linking or connecting the coupling to a circulatory assist device, such as an artificial heart.

In use, the muscle is generally prepared to attachment to the coupling. The filaments of the second portion are embedding into the muscle at or adjacent the terminal or distal end. Preferably the filaments are gathered into a plurality of tows, swagged into a needle, and sewn into the muscle. The tows can be sewn through the muscle obliquely at least two, and preferably three times, in a S-shaped pattern. A sheath is infolded to cover a portion of the strand, preferably where the strand has been embedded with the sheath.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

DETAILED DESCRIPTION OF THE INVENTION

Figure 1:
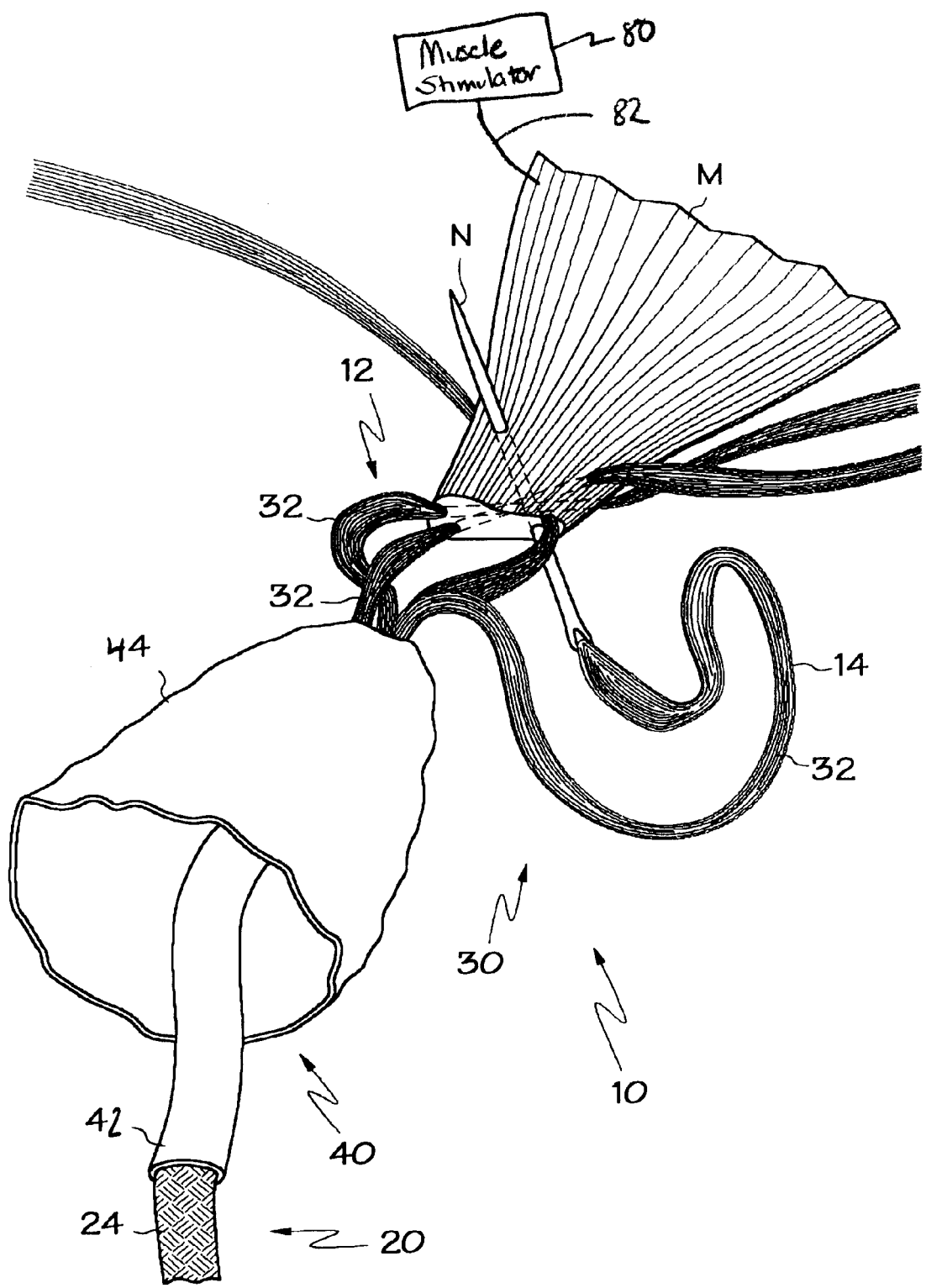
FIG. 1 is perspective view of the linkage made in accordance with the present invention being attached to the distal end of skeletal muscle.
Figure 2:
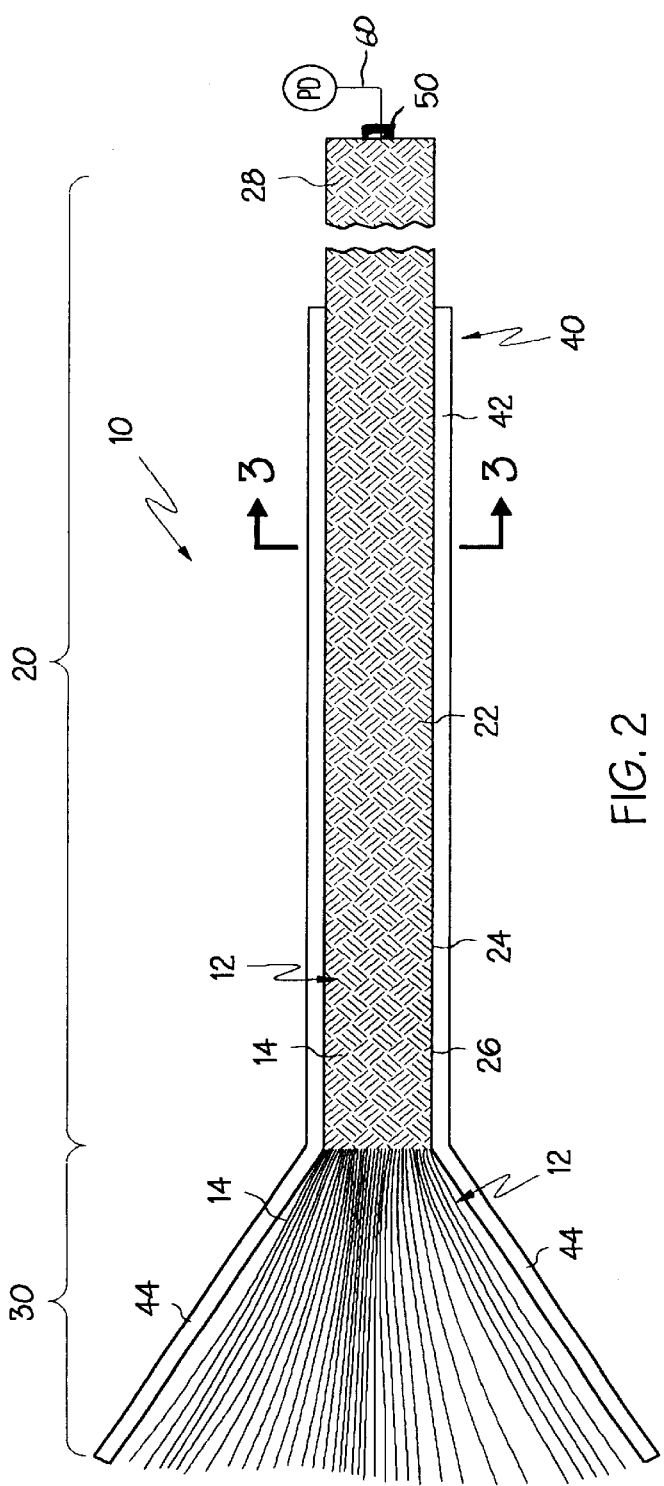
FIG. 2 is longitudinal sectional view of a linkage made in accordance with the present invention.
Figure 3:
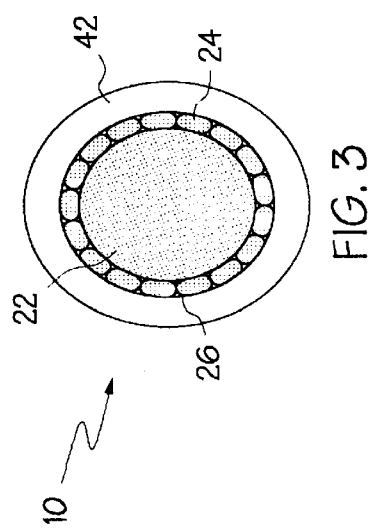
FIG. 3 is cross sectional view of the device taken along line 3—3 in FIG. 2.

Referring now to the figures in detail wherein like numerals indicate the same elements throughout the views, the present invention includes a prosthetic coupling generally identified as 10 for utilizing skeletal muscle, preferably left generally in situ, to power or actuate a circulatory assist device, such as an artificial heart. Coupling 10 can include a strand 12 or suture, which can have thousands of fine individual filaments 14 or fibers, for repeatedly and indefinitely transmitting the contractile force of skeletal muscle to a prosthetic device. The filaments 14 used with the present invention should be configured so that removal of the filament 14 from the muscle, once embedded, is not easy accomplished. Also, the filament 14 of the present invention preferably should be capable integrating or of forming a bond with the skeletal muscle to sustain the force caused by linear shortening of the muscle, which can be greater than 40 N, and in some cases greater than 80 N. Also, the filaments 14 should be configured to assist in maximizing the potential surface area of the strand 12, which thereby enhances tissue integration into and around the filaments 14, as will be detailed below, and also can permit the transfer of increased power via coupling 10. To increase the surface area of the strand 12, the filaments 14 should have a sufficiently small diameter. In one embodiment, each filament 14 can have a diameter of less than about 40 microns, and preferably less than 10 microns.

Filaments 14 are preferably made of a material that does not dissolve when placed in the body over time and can withstand lateral compressive and shear forces applied by muscle tissue as it contracts, and thus, moves the embedded filaments (e.g., 14). The material of the filament 14 should also have a coefficient of friction to assist in preventing the filaments 14 from becoming unembedded in the muscle M and thus, removed. Preferred materials of the filament 14 should also be porous or textured to further increase the coefficient of friction, enlarge the surface area of filament 14, and/or enhance tissue integration in and around the filament 14 whereby the filament 14 is not easily removed from the muscle M. Illustrative examples of materials which may be suitable as filaments 14 includes bulk polymers such as, polyolefins (e.g., high molecular weight polyethylenes and/or very high molecular weight polypropylenes), polytetrafluroethylene (PTFE), and the like.

The coupling 10 of the present invention has at least two portions, a first or prosthetic attachment portion 20 and a second or muscle coupling portion 30. The filaments 14 are generally organized differently for use in the present invention.

In prosthetic attachment portion 20, the filaments 14 are preferably configured and organized so as to assist in attaching the coupling 10 to a prosthetic device, such as a circulatory assist device. The organization and configuration of the prosthetic attachment portion 20 should assist in reducing the extensibility and/or elastic nature of the strand 12, and thus, minimizing the energy dissipation along the length of strand 12. Preferably, the prosthetic attachment portion 20 should be extendable only about 1% to 2% of its overall length when subjected to the expected force. A kernmantel type or compact cord can be used as prosthetic attachment portion 20 to assist in efficiently transmitting lateral contraction forces from a muscle, or group of muscles, to a bone or prosthetic device.

The prosthetic attachment portion 20 preferably includes a core portion 22 having a plurality of filaments 14 bundled and extending generally parallel to each along the length of the coupling 10. The outer filaments 24 can be organized to provide mechanical stability and structural integrity to the first portion 20. For example, the outer filaments 24 can be gathered into several groups or bundles 26, and then braided around the core portion 22 to provide a jacket around the core portion 22. In one embodiment, about 40 percent, and preferably about 10 percent, of all the filaments 14 can be gathered into several, such from about 8 to about 16, small bundles 26 and braided around the core portion 22 to provide the desired kernmantel type cord preferred for use with the present invention.

The distal portion 28 of the prosthetic attachment portion 20 can be provided with a junction device 50, such as a connector, clamp, or other mechanical linkage configured to assist in connecting or coupling the coupling 10 to mechanical linkages 60 (e.g., hydraulic cylinders and pistons, sheathed cables, pulleys and the like) of the prosthetic device, such as the circulatory assist device PD. The prosthetic device should provide assistance in the maintenance of blood flow and circulation though a body's circulation system. Illustrative examples of circulatory assist devices that may be suitable for use can include an intraventricular pump, such as the device disclosed in U.S. Pat. No. 5,139,517 (Corral), an artificial heart that entirely replaces that existing natural heart, such as the device disclosed in U.S. Pat. No. 4,904,225 (Chareire, et al.), a cardiac assist device used with the natural heart, such as the device that is discloses in U.S. Pat. Nos. 2,826,193 (Vineberg), 3,455,298 (Anstadt) and/or 4,536,893 (Parravicini), a ventricular assist device, such as the device disclosed in U.S. Pat. No. 4,690,134 (Snyders), and/or a heart harness pump, such as the devices disclosed in PCT Publication WO 97/24101 (Melvin), the disclosures of which are hereby incorporated herein by reference. Preferably, the prosthetic devices should also be configured to assist in maintaining the force developed by the skeletal muscle's contraction throughout the ejection stroke of the prosthetic device without additional metabolic demands on the skeletal muscle. Illustrated examples of such devices used with a prosthetic device can include ratches, valves, and the like.

The second or muscle coupling portion 30 of the coupling 10 is provided generally so as to assist with integration into and/or maintenance of the filaments 14 within the muscle tissue M. Muscle coupling portion 30 preferably can include a plurality of generally unbraided, unspun, untwisted and unplaited filaments 14 for maximizing the surface area of the strand 12 of the muscle coupling portion 30. Filaments 14 of the muscle coupling portion 30 should have a length sufficient so they can be dispersed about the distal or terminal portion of the muscle M so that the muscle's contraction generates low pressure on the filaments 14. Also, the length, and thus its overall surface area, of filaments 14 should be such that the sum of any shear forces on a filament 14 would sustain the required tensile force on the filament 14 in the presence of hydrostatic pressure in the muscle tissue. A suitable filament 14 for use with the present invention can have a length greater than 40 mm.

A sheath or sleeve 40 can be provided over the strand 12 so as to assist in inhibiting fibrous tissue from adhering to the coupling 10 and thus, interfering with its function and/or generally linear movement. The sleeve 40 can include a tube-shaped portion 42 that partially or entirely covers, and preferably surrounds or encases, at least a portion of the prosthetic attachment portion 20. It is contemplated that the exterior surface of the prosthetic attachment portion 20, and preferably the outer filaments 24 may be formed from a fiber(s) or material(s) that assists in resisting tissue integration, which can be different from the filaments 14 of the muscle coupling portion 30. The sleeve 40 can also include an invertible generally frustoconically shaped portion 44 that can be positioned or unfolded around the portion of the muscle M in which the second portion 30 is embedded. The generally frustoconically shaped portion 44 preferably has a corrugated configuration so as to assist in allowing for radial and/or axial expansion and contraction of the muscle M as it contracts and relaxes. Illustrative examples of material which may be employed as sleeve can include polyurethane, such as that provided under the brand name Tecoflex by Thermocardio Systems of Woburn, Mass.

Open heart thoracic surgery may be required to implant the circulatory assist device PD. Alternatively, intracardiac components of the circulatory assist device may be placed and positioned by wall penetrating needles and/or insertion of components through the left atrial appendage of a beating heart. Clinically sufficient anesthesia is administered and standard cardiac monitoring is employed to the patient and then, the thoracic cavity, where the heart is usually situated, is opened using standard thoracic surgical procedures, which are known to those skilled in the art.

Once the thoracic cavity is opened, if an open heart procedure employed in the present invention, circulation of blood to the natural heart should be bypassed so the present invention can be inserted on and/or into the patient. The superior vena cava, the inferior vena cava, and aorta are cannulated. The circulatory system is connected to as a cardiopulmonary bypass machine so that circulation and oxidation of the blood are maintained during the surgical procedure.

When using an artificial heart, the natural heart is removed and replaced by an artificial heart, such as the one disclosed in U.S. Pat. No. 4,904,225 (Chareire, et al), the disclosure of which is hereby incorporated herein by reference. When retaining the natural heart and using an assist device, the assist device, such as an intraventricular pump, a ventricular assist device or a heart harness, are positioned in and/or around the natural heart, as desired.

The skeletal muscle for use with the present invention should be nonessential to other vital or important body functions. Moreover, the skeletal muscle should be capable of developing enough power or force to power a circulatory assist device without showing fatigue that could decrease energy output. Illustrative examples of skeletal muscle which may be suitable in the present invention include a dorsal muscle, such as the latissimus dorsi muscle, an abdominal muscle, such as one or both of the psoas major muscles, a ventral muscle, such as the rectus abdominis muscle, or a muscle from a lower limb, such as the gracilis or the vastus lateralis muscles.

The detached end of the muscle M is prepared for attachment to the coupling 10, preferably by still allowing the muscle M to operate in its normal line of action with disturbing its blood supply. The terminal or distal end of the muscle M selected can be dissected and disconnected at or adjacent its musclotendious junction using standard surgical techniques. The skeletal muscle for use with the present invention is also preferably conditioned, such as with a low frequency stimulation so that the muscle becomes conditioned as fatigue resistant muscle.

The filaments 14 of the second portion 30 can be gathered into a plurality of easily separable tows or bundles 32, and then swagged into an instrument for sewing an/or embedding the filaments 14 into the muscle, such as a tapered needle N (either straight or curved) or other surgical instrument. Each bundle 32 is then sewn or woven into the terminal portion of muscle M in a distribution pattern so that the tension on the filaments 14 will affect lateral compressive forces on the muscle M during its contraction that will sum with the interstitial pressure during muscle contraction. The distribution pattern of filaments 14 should also be such that muscle tissue is interposed between the filaments 14 and such that the sum of the shear forces on the filaments 14 would sustain tensile forces while maintaining hydrostatic pressure and normal forces at or below normal physiological values. A sinusoidal pattern or an oblique S shaped pattern can assist in satisfying these conditions and also can assist to enhance filament 14 integration in the muscle M and insinuation of muscle tissue between the filaments 14.

Once the filaments 14 have been woven or sewn into the muscle M, the needle can then be cut off from each tow, and the bundles and filaments 14 tied off using technique known in the industry. The other end of the coupling 10 can be attached and/or secured to a prosthetic device PD using a mechanical linkage device, such as a clamp, so that the muscle M can actuate it using coupling 10. Attachment of coupling 10 to the prosthetic device can be accomplished using apparatus and techniques known in the industry.

The inverted frustoconically shaped portion 44 of the sleeve 40 can be unfolded, positioned or straightened out to generally envelopes a portion of the terminal end of the muscle M. Covering the portions or areas of the muscle M with sleeve 40, and preferably the frustoconically shaped portion 44, where filaments 14 protrude can reduce the possibility of scar tissue formation. Moreover, portion 44 can be trimmed so that only the exposed filaments 14 remain covered thereby assisting to decrease the expected healing/integration time of the filaments 14. By trimming the sleeve 40, and preferably the frustoconically shaped portion 44, fluids and/or blood can drain away from the incisions of filaments 14 into the muscle M, and thus be absorbed by surround tissue. Also, by trimming the frustoconically shaped portion 44, the potential for kinking of the sleeve 40 during muscle contraction is reduced. The frustoconically shaped portion 44 can also be attached or tacked to the muscle M to prevent movement by sewing small sutures in the portion 44 and the muscle M.

A muscle stimulator 80, such as a pulse generator, is preferably implanted and attached to the body. An electrical lead 82 of the stimulator 80 is preferably attached at or adjacent the muscle motor nerve for assisting in stimulating the skeletal muscle M so that it contracts, as desired.

Cardiotomies are closed, and the coupling 10 is attached to the circulatory assist device PD.

Once the circulatory assist device PD is properly positioned and secured, termination of a cardiopulmonary bypass, if used, is attempted and, if successful, the thoracotomy is closed.

An alternative method for positioning the present invention can include removing the natural heart from the patient, positioning all the components of the circulatory assist device PD as discussed above, and auto-transplanting the natural heart back into the patient using standard cardiectomy and cardiac transplant techniques known in the industry.

Alternatively, it is contemplated that the coupling 10 of the present invention could also be used as an artificial tendon to connect muscle to bone.

Having shown and described the preferred embodiments to the present invention, further adaptations of the activation device for the living heart as described herein can be accomplished by appropriate modifications by one of ordinary skill in the art without departing from the scope of the present invention. For example, the present invention can be used as an artificial tendon to connect muscle to bone. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. A prosthetic coupling for use with skeletal muscle having a longitudinal axis, said coupling comprising:
    a plurality of longitudinally extending filaments forming a strand, said strand having a first portion and a second portion,
    the first portion comprising a core portion wherein the filaments extend generally parallel to each other, and an exterior portion wherein the filaments are braided along the longitudinal axis around the core portion, and
    wherein the filaments of said second portion are arranged in a plurality of tows.

2. The device of claim 1, wherein said filaments comprise a polyester fiber.

3. The device of claim 1, wherein said filaments have a diameter less than about 40 microns.

4. The device of claim 3, wherein said filaments have a diameter less than about 10 microns.

5. The device of claim 1, wherein said coupling comprises greater than about 5000 filaments.

6. The device of claim 1, wherein the length of the filaments of the second portion is greater than about 40 mm.

7. The device of claim 1, comprising a sheath for covering a portion of the strand.

8. The device of claim 6, wherein said sheath comprises a frustoconically shape configured for covering a portion of the muscle.

9. The device of claim 1, wherein said strand comprises a junction device adjacent the end of the first portion and configured for attachment to a prosthetic device.

10. The device of claim 1, wherein said filaments extend substantially along the entire length of the strand.

11. An assembly for powering a prosthetic device with skeletal muscle, said assembly comprising:

a coupling having a plurality of longitudinally extending filaments forming a strand, said strand having a longitudinal axis, a first portion and a second portion, the first portion having a distal end and comprising a core portion wherein the filaments extend generally parallel to each other, and an exterior portion wherein the filaments are braided along the longitudinal axis around the core portion, and wherein the filaments of said second portion are arranged in a plurality of unbraided tows;

a junction device secured to said coupling adjacent the distal end of the first portion; and a circulatory assist device linked to the junction device.

12. The assembly of claim 11, comprising a muscle stimulator having an electrical lead, wherein the electrical lead is attached to the muscle.

13. The assembly of claim 11, wherein the circulatory assist device comprises a mechanical linkage configured for translating mechanical energy to hydraulic energy.

14. The assembly of claim 11, wherein said filaments extend substantially along the entire length of the strand.

15. A method for coupling a muscle to a prosthetic device, comprising the steps of:

(A) providing a coupling having a longitudinal axis, said coupling comprising:

a plurality of longitudinally extending filaments forming a strand, said strand having a first portion and a second portion, the first portion comprising a core portion wherein the filaments extend generally parallel to each other, and an exterior portion wherein the filaments are braided along the longitudinal axis around the core portion, and wherein the filaments of said second portion are arranged in a plurality of tows;

(B) embedding said tows into the muscle; and (C) attaching the first portion of the coupling to the prosthetic device.

16. The method of claim 15, wherein each of said tows is swagged to a needle, and wherein said step of embedding said tows into the muscle comprises:

sewing each of the tows into the muscle.

17. The method of claim 16, wherein said tows are sewn through the muscle obliquely at least two times in an S-shaped pattern.

18. The method of claim 15, further comprising providing an invertible sheath to cover a portion of said strand;

covering the portion of the muscle where the strand has been embedded with the sheath.

19. The method of claim 15, comprising the steps of:

providing a circulatory assist device; and connecting the skeletal muscle to the circulatory assist device using the coupling.

20. The method of claim 15, comprising the steps of:

providing a muscle stimulation device: and connecting the muscle stimulation device to the skeletal muscle.

21. The method of claim 15, comprising the step of reconditioning the skeletal muscle so that the muscle is a fatigue resistant muscle.

22. The device of claim 1, wherein each of said tows is swagged to a surgical instrument suitable for embedding the filaments of the second portion into muscle.

* * * * *

UNITED STATES PATENT AND TRADEMARK OFFICE
CERTIFICATE OF CORRECTION

PATENT NO. : 6,214,047 B1
DATED : April 10, 2001
INVENTOR(S) : David B. Melvin

It is certified that error appears in the above-identified patent and that said Letters Patent is hereby corrected as shown below:

Claim 8,
Line 1, replace "6" with -- 7 --.

Claim 18,
Line 2, after "strand:" insert the word -- and --.

Signed and Sealed this

Sixth Day of November, 2001

Attest:

NICHOLAS P. GODICI
Attesting Officer    Acting Director of the United States Patent and Trademark Office